United States Patent [19]
Hahn et al.

[11] Patent Number: 4,885,396
[45] Date of Patent: Dec. 5, 1989

[54] PROCESS FOR THE PREPARATION OF 2-HYDROXY-4-(2'-HYDROXYETHOXY) BENZOPHENONES

[75] Inventors: Erwin Hahn, Heidelberg; Peter Neumann, Wiesloch, both of Fed. Rep. of Germany

[73] Assignee: BASF Aktiengesellschaft, Ludwigshafen, Fed. Rep. of Germany

[21] Appl. No.: 197,042

[22] Filed: May 20, 1988

[51] Int. Cl.$^4$ ............................................... C07C 45/71
[52] U.S. Cl. ..................................... 568/315; 568/314
[58] Field of Search ................................ 568/314, 315

[56] References Cited
U.S. PATENT DOCUMENTS 2,987,555  6/1961  Davis .................................... 568/644
4,261,922  4/1981  Kim ...................................... 568/315
4,310,708  1/1982  Strege .................................. 568/608
4,314,086  2/1982  Soula et al. ......................... 568/315
4,341,905  7/1982  Strege .................................. 568/608

OTHER PUBLICATIONS

Starks et al., "Phase Transfer Catalysts", pp. 64–65, (1978).

Primary Examiner—James H. Reamer
Attorney, Agent, or Firm—William G. Conger; Joseph D. Michaels

[57] ABSTRACT

A process for the preparation of 2-hydroxy-4-(2'-hydroxyethoxy)benzophenones, by reacting 2,4-dihydroxybenzophenones with ethylene carbonate in the presence of a quaternary ammonium salt catalyst at elevated temperatures, and isolating the finished product from the crude reaction mixture.

13 Claims, No Drawings

PROCESS FOR THE PREPARATION OF 2-HYDROXY-4-(2'-HYDROXYETHOXY) BENZOPHENONES

BACKGROUND OF THE INVENTION

1. Field of the Invention

This invention deals with a novel process for the preparation of 2-hydroxy-4-(2'-hydroxyethoxy)benzophenones having a structure (FIG. I)

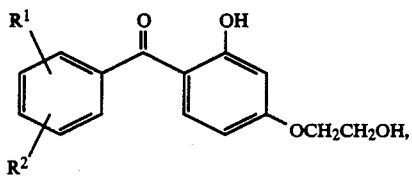

wherein $R^1$ and/or $R^2$ may be hydrogen, hydroxyl, hydroxyethoxy, fluorine, chlorine, bromine, cyanide, $C_1$–$C_8$ alkyl or alkoxy; a $C_4$–$C_7$ cycloalkyl; a $C_1$–$C_4$ alkyl substituted with one or more fluorine, chlorine or bromine atoms; or a phenoxy, benzyl, or phenyl substituted with fluorine, chlorine, bromine, a $C_1$–$C_4$ alkyl, or a $C_1$–$C_4$ alkoxy.

The process is carried out by reacting 2,4-dihydroxybenzophenones (FIG. II),

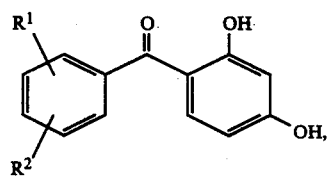

for which $R^1$ and $R^2$ may be any of the substitutes described for FIG. I, with ethylene carbonate in the presence of a catalyst at elevated temperatures. The reaction product is subsequently isolated from the reaction mixture.

2. Description of the Prior Art

There are a number of publications which address the synthesis of the subject compound. Eggensperger discloses in U.S. Pat. No. 3,676,471, a method wherein 2-hydroxy-4-(2'-hydroxyethoxy)benzophenones may be prepared by ethoxylating 2,4-dihydroxybenzophenones with either ethylene oxide or with ethylene carbonate in the presence of basic catalysts, preferably alkali carbonates, alkali earth carbonates or alkali alkolates. This method however has a number of disadvantages. It requires the use of solvents, particularly ketones. Because of the basic nature of the reaction mixture only substantially inert ketones such as diisobutyl ketone may be employed. When ethylene carbonate is the alkoxylating agent, it must be used in large excess with a correspondingly high concentration of an auxiliary base. The above contributes significantly to the cost of the process. Further, Example 1 discloses that the reaction product is obtained by extraction with a chlorinated hydrocarbon. Halogenated hydrocarbons present problems because they are toxic and potential envrionmenal hazards.

U.S. Pat. Nos. 4,261,922 and 4,341,905 claim the use of potassium and/or general alkali metal halogen salts as catalysts used under neutral conditions to avoid side reactions.

U.S. Pat. No. 4,310,708, discloses the use of phosphonium salts as catalysts. The process also discloses a reaction exhibiting good selectivity, that may be carried out in an inert organic solvent, but preferably in the absence of said organic solvent. The use of phosphonium salts as a catalyst is undesirable because of the environmental hazard they pose.

The Bulletin of the Chemical Society of Japan, Vol. 46, 553–556 (1978), discloses the use of tetraethylammonium halogens as catalysts, but only with monofunctional phenols as reactants.

THE SUMMARY OF THE INVENTION

The purpose of the invention was to develop an economical, environmentally responsible process for the preparation of 2-hydroxy-4-(2'-hydroxyethoxy)benzophenones by the selective ethoxylation of 2,4-dihydroxybenzophenones.

Accordingly a process was developed for the preparation of 2-hydroxy-4-(2'-hydroxyethoxy)benzophenones having a structure (FIG. I), wherein $R^1$ and/or $R^2$ may be hydrogen, hydroxyl, hydroxyethoxy, fluorine, chlorine, bromine, cyanide, $C_1$–$C_8$ alkyl or alkoxy; $C_4$–$C_7$ cycloalkyl; a $C_1$–$C_4$ alkyl, substituted with one or more fluorine, chlorine or bromine atoms; or a phenoxy, benzyl, or phenyl substituted with fluorine, chlorine, bromine, a $C_1$–$C_4$ or a $C_1$–$C_4$ alkoxy.

The process is carried out by reacting 2,4-dihydroxybenzophenones as described by FIG. II with ethylene carbonate in the presence of a catalyst, preferably a quaternary ammonium salt, at elevated temperatures. The product (FIG. I) is subsequently isolated from the reaction mixture.

DETAILED DESCRIPTION OF THE INVENTION

According to the process of the invention a number of 2,4-dihydroxy compounds may be employed as a reactant. Thus, $R^1$ and/or $R^2$ may be stand for hydrogen, hydroxyl, hydroxyethoxy, fluorine, chlorine, bromine, cyanide, a $C_1$–$C_8$ alkyl or an alkoxy such as methyl, ethyl, propyl, butyl, isobutyl, t-butyl, pentyl, hexyl, heptyl, octyl or the corresponding alkoxy radials; a $C_4$–$C_7$ cycloalkyl such as cyclobutane, cyclopentane, cyclohexane, or cycloheptane. In addition $R^1$ and/or $R^2$ may be a $C_1$–$C_4$ alkyl group substituted by one or more fluorine, chlorine, or bromine atoms, e.g. trifluoromethyl or 1,2-dichloroethyl, or $R^1$ and/or $R^2$ can be phenoxy, benzyl, or phenyl whereby the aromatic radicals cited possess inert substitutes such as fluorine, chlorine, bromine or $C_1$–$C_4$ alkyl radical or an alkoxy radical. In view of using the final product (FIG. I) as a light stabilizing agent, of particular significance are starting materials (FIG. II) in which $R^1$ is in the ortho position relative to the carbonyl group and whereby $R^1$ stands for a hydroxyl group. Of significance also are starting materials (FIG. II) in which $R^1$ and $R^2$ stand for hydrogen or in which $R^1$ is an ortho-hydroxyl group and in which $R^2$ is a para-hydroxyl group. When employing quaternary ammonium salts as catalysts in the process of this invention, one avoids the ethoxylation of the ortho-hydroxyl groups, predominantly. Hydroxyl groups are ethoxylated in the meta or para positions.

Specific examples of starting materials (FIG. II) are: 2,4-dihydroxybenzophenones, in which $R^1$ is hydrogen or hydroxy and in which $R^2$ is hydrogen, methyl, ethyl, propyl, isopropyl, butyl, methyoxy, ethoxy, propoxy, O—C₆H₁₃, O—C₈H₁₇, phenoxy, fluorine, chlorine, bromine, cyanide, trifluoromethyl or benzyl, whereby the substitute cited can be in the ortho-, meta- or para-positions relative to the carbonyl groups.

The 2,4-dihydroxy compounds (FIG. II) used as starting materials are well known, or are able to be prepared in a conventional fashion, e.g. by the Friedel-Crafts-Acylation of resorcin with carboxylic acid chlorides having the following structure (FIG. II):

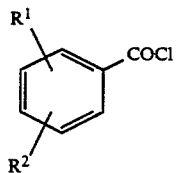

in which R¹ and R² possess the meaning listed for starting material (FIG. II).

The reaction of 2,4-dihydroxybenzophenone (FIG. II) with ethylene carbonate can take place in the presence of solvents which are inert to the reactants, for example in ethers such as diethyleneglycol dimethylether or anisol, yet preferably is carried out solvent-free. Ethylene carbonate can be used in equal molar quantities to FIG. II, in less than equal molar quantities or preferably in a slight excess. One generally uses from 0.95 to 1.5 moles of ethylene carbonate per mole of dihydroxybenzophenone (FIG. II). Larger quantities are possible, yet there are no additional advantages in using them.

Typical quaternary ammonium salts are practically all compounds of the type which are known from phase transfer reactions see for example E. V. Dehmlow and S. S. Dehmlow, *Phase Transfer Catalysis*, 2nd edition 1983. Examples are ammonium compounds having the structure (FIG. III),

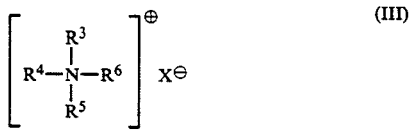

in which radicals R³ through R⁶ are the same or different and are C₁-C₁₈ alkyl radicals. Two of the radicals, R³ and R⁴ in addition can stand for a C₅ or C₆ cycloalkyl radical, i.e. a cyclopentyl radical or a cyclohexyl radical or they can stand for phenol. R³ and R⁴ and/or R⁵ can also stand for benzyl radicals. Furthermore, radicals R³ and R⁴ together can join to form a 5 or 6 membered ring and together with the nitrogen to which they are bound they can form a pyrrolidone, piperidine, pyrol or pyridine system.

Examples of ions with opposite charges, X⁻ in FIG. III, are preferably anions of organic or inorganic acids. Examples are the anions F⁻, Cl⁻, Br⁻, I⁻, CN⁻, SCN⁻, NO₃⁻, OH⁻, acetate, benzoate or sulfonates such as toluene-4-sulfonate or trifluoromethane sulfonate. In addition less nucleophilic anions such as HSO₄⁻ and H₂PO₄⁻ are also examples.

Due to the overall suitability of the ammonium salts, the selection of a catalyst is governed primarily by its availability and price. Therefore one normally uses primarily ammonium halides such as iodides, bromides or chlorides. On account of their good access ability, tetraalkylammonium salts or ammonium salts in which three of the radicals are lower molecular alkylradicals and the fourth radical is benzyl or a C₆ to C₁₈ alkylradical are preferred.

The following are examples of ammonium compounds which may be used as catalysts: benzyldimethyldodecylammonium bromide, benzyldimethylhexadecylammonium chloride, benzyldimethyltetradecylammonium chloride, benzyltributylammonium bromide, benzyltributylammonium chloride, benzyltriethylammonium iodide, benzyltrimethylammonium bromide, benzyltrimethylammonium chloride, benzyltrimethylammonium fluoride, benzyltrimethylammonium hydroxide, benzyltrimethylammonium ethoxide, dodecylethyldimethylammonium bromide, ethylhexadecyldimethylammonium bromide, hexadecyltrimethylammonium bromide, hexadecyltrimethylammonium chloride; methyltrioctylammonium bromide, methyltrioctylammonium chloride, methyltrioctylammonium iodide, octadecyltrimethylammonium bromide, phenyltrimethylammonium bromide, phenyltrimethylammonium chloride, phenyltrimethylammonium hydroxide, tetrabutylammonium bromide, tetrabutylammonium chloride, tetrabutylammonium hydroxide, tetrabutylammonium iodide, tetrabutylammonium methane sulfonate, tetrabutylammonium rhodanide, tetrabutylammonium toluene-4-sulfonate, tetrabutylammonium trifluoromethane sulfonate, tetradecyl trimethylammonium bromide, tetradodecylammonium bromide, tetraethylammonium acetate, tetraethylammonium bromide, tetraethylammonium chloride, tetraethylammonium cyanide, tetraethylammonium fluoride, tetraethylammonium hydroxide, tetraethylammonium iodide, tetraethylammonium rhodanide, tetraethylammonium toluene-4-sulfonate, tetraethylammonium trifluoromethane sulfonate, tetraheptylammonium bromide, tetrahexylammonium benzoate, tetrahexylammonium bromide, tetrahexylammonium chloride, tetrahexylammonium iodide, tetrakis(decyl)ammonium bromide, tetramethylammonium bromide, tetramethylammonium chloride, tetramethylammonium hydroxide, tetramethylammonium iodide, tetramethylammoniumtoluene-4-sulfonate, tetraoctadecylammonium bromide, tetraoctylammonium bromide, tetrapentylammonium bromide, tetrapentylammonium iodide, tetrapropylammonium bromide, tetrapropylammonium hydroxide, tetrapropylammonium iodide, tributylheptylammonium bromide, tributylmethylammonium bromide, tributylmethylammonium chloride, tributylmethylammonium hydroxide, tributylmethylammonium iodide, trioctylmethylammonium chloride, and triethylmethylammonium bromide.

The quantity of catalyst is not particularly critical. Generally one can use from 0.1 to 0.001, more preferably from 0.02 to 0.05 moles of catalysts per mole of starting material (FIG. II). Larger quantities, 0.25 moles, are possible yet are not required.

The reaction temperature is ordinarily from 100° C. to 210° C., more preferably 120° C. to 200° C. For achieving a satisfactory reaction rate, temperatures above 140° C. are preferred. Possible side reactions are generally avoided below 180° C. Therefore the optimum temperature range is regarded to be from 140° C. to about 175° C. Generally the reaction times range from about 2 to about 12 hours.

Finishing the crude reaction mixture and isolating 2-hydroxy-4-(2'-hydroxyethoxy)benzophenones can occur in a conventional fashion, after the carbon dioxide development has terminated, by the addition of water or an organic solvent such as alcohols, and then by crystallizing or distilling the final product (FIG. I). If desired, one can also add activated carbon or bleaching earth to the crude reaction mixture.

The product (FIG. I) prepared according to the process of the invention is suitable for use as light stabilizing agents, for the light stabilization of organic materials, preferably plastics and coatings.

In view of their use as light stabilizers, preferred compounds are:

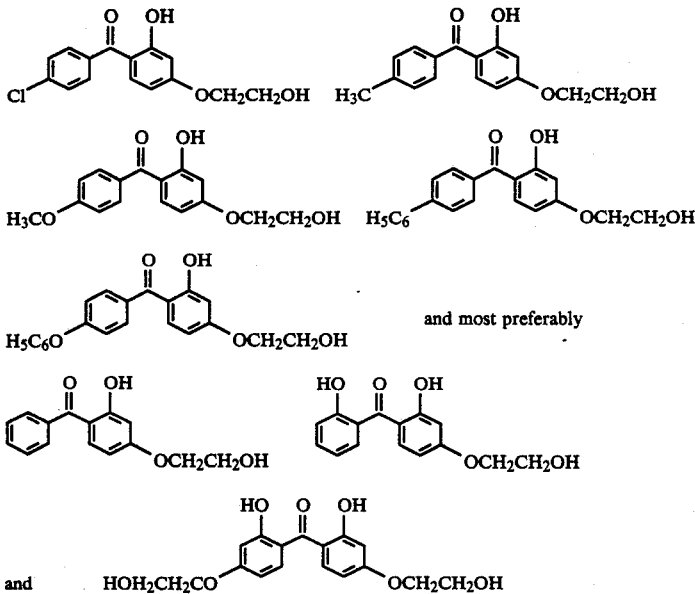

and most preferably

Generally the finished materials (FIG. I) prepared according to said process precipitate out in sufficient purity, however an additional simple purification step may be added to the finishing process. Good quality 2-hydroxy-4-(2'-hydroxyethoxy)benzophenones are obtained when water is added to the reaction mixture upon completion. Then the pH is adjusted to about 10–12 using an alkali such as sodium hydroxide and the reaction mixture is restirred for a short time (about 1 to 2 hours), preferably while heating to temperatures of from 90° C. to 100° C. The reaction product (FIG. I) is subsequently precipitated by acidifying the mixture to a pH of about 7 to 8, by adding minerals acids such as diluted hydrochloric acid or sulfuric acid. When using ammonium iodides it may be advantageous to add a diluted sodium hydrogen sulfite solution after diluting the reaction with water.

The following examples illustrate the various aspects of the invention but are not intended to limit its scope. Where not otherwise specified throughout this specification and claims, temperatures are given in degrees centigrade and parts, percentages and proportions are by weight.

EXAMPLE 1

A mixture of 214 parts (1 mole) of 2,4-dihydroxybenzophenone, 100 parts (1.125 mole) of ethylene carbonate and 5.7 parts (0.025 mole) of benzyltriethylammonium chloride was heated while stirring to 140° C. to 150° C. at which point carbon dioxide began to evolve slowly. After the evolution of carbon dioxide stopped (11 hours) the reaction mixture was cooled to about 100° C. and then within 5 minutes 750 ml of water was added while stirring. The mixture was cooled to room temperature while stirring, at which point the oily reaction product crystallized. After suctioning off the solid, washing with water, and drying; 2-hydroxy-4-(2'-hydroxyethoxy)benzophenones was obtained having purity of 97 percent (HPLC). Yield: 248 parts (93 percent of the theoretical).

EXAMPLE 2

Following the procedure of Example 1, one obtained 2-hydroxy-4-(2'-hydroxyethoxy)benzophenone (98 percent of the theoretical) from 21.4 parts (0.1 mole) of 2,4-dihydroxybenzophenone, 11 parts (0.125 mole) of ethylene carbonate and 10 parts (0.025 mole=25 mole percent) of tetrabutylammonium iodide after a reaction time of 2 hours.

EXAMPLE 3

Following the procedure in Example 1, one obtained 232 parts of 2-hydroxy-4-(2'-hydroxyethoxy)benzophenone (90 percent of the theoretical) from 214 parts (1 mole) of 2,4dihydroxybenzophenone, 100 parts (1.125 mole) of ethylene carbonate and 2.28 parts (0.01 mole) of benzyltriethylammonium chloride, after diluting with 1,000 ml of water.

EXAMPLE 4

Follow the procedure in Example 1, except after completing the reaction, the reaction mixture was treated with 900 ml of methanol and 5 parts of activated charcoal then it was stirred for 2 hours at 50° C., filtered, and the filtrate was treated proportionately with 1000 ml of water and 500 parts of ice. The pH was adjusted to 4–5 by the addition of dilute sulfuric acid, then the precipitate was suctioned off, washed with water and dried. Yield: 200 parts (77.5 percent of the theoretical).

EXAMPLE 5

A mixture of 21.4 parts (0.1 mole) of 2,4-dihydroxybenzophenone, 9.7 parts (0.11 mole) of ethylene carbonate and 1.9 parts (0.005 mole) hexadecyltrimethylammonium bromide was heated for 11 hours at 150° C. to 160° C. The reaction was cooled to about 100° C. and water was added, the pH was adjusted to about 7.5-8 using a small amount of dilute sodium hydroxide. The reaction mixture was stirred an additional 3 hours and the precipitate was suctioned off. After washing and drying 22 parts of 2-hydroxy-4-(2'-hydroxyethoxy)-benzophenone (85 percent of the theoretical) was obtained.

EXAMPLE 6

214 parts (1 mole) of 2,4-dihydroxybenzophenone, 88 parts (1 mole) of ethylene carbonate and 9 parts (0.025 mole) of tetrabutylammonium iodide were heated for 8 hours at 150° C. to 155° C. The reaction product was treated in the same manner as Example 5. Yield: 237 parts (91 percent of the theoretical).

EXAMPLE 7

428 parts (2 mole) 2,4-dihydroxybenzophenone, 200 parts (2.25 mole) of ethylene carbonate and 22.8 parts (0.1 mole) of benzyltriethylammonium chloride were prepared as in Example 1. After diluting with 1500 ml of water and cooling while stirring, the pH was adjusted to 11 using dilute sodium hydroxide, next it was stirred 1 hour at 90° C. to 100° C. and then after cooling to room temperature the pH was lowered to about 7.5-8 by the addition of dilute hydrochloric acid. The precipitate was suctioned off, washed with water, and dried. Yield: 481 parts (93 percent of the theoretical).

EXAMPLES 8-11

Prepared as in Example 1, the 2,4-dihydroxybenzophenones ($R^1$=H) listed in the following table were reacted. The products were characterized by their melting points.

TABLE I

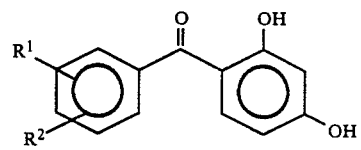

(II)

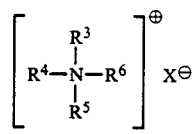

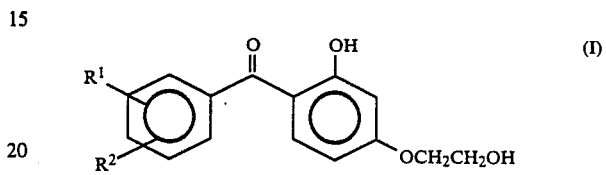

(I)

| Example | $R^2$ | Melting Point (I) [°C.] | Yield[a] [% of theoretical] |
|---|---|---|---|
| 8 | $CH_3$ | 128-130 | 70 (recrystallized from toluene) |
| 9 | $OCH_3$ | 143-146 | 79 (recrystallized from ethanol) |
| 10 | Cl | 122-124 | 91 |
| 11 | $OC_6H_5$ | 96-98 | 89 |

[a]not optimized

The embodiments of the invention in which an exclusive privilege or property is claimed are defined as follows:

1. A process for the preparation of 2-hydroxy-4-(2,-hydroxyethyoxy)benzophenones having a structure (FIG. I), wherein either R group is hydrogen, hydroxyl, hydroxyethoxy, fluorine, chlorine, bromine, cyanide; a $C_1$-$C_8$ alkyl; a $C_1$-$C_8$ alkoxy; a $C_4$-$C_7$ cycloalkyl; a $C_1$-$C_4$ alkyl, substituted with one or more fluorine, chlorine or bromine, or one of the following phenoxy, benzyl or phenyl substituted by fluorine, chlorine, bromine, a $C_1$-$C_4$ alkyl, or a $C_1$-$C_4$ alkoxy comprising: reacting a 2,4-dihydroxybenzophenone having a structure (FIG. II), wherein $R^1$ and $R^2$ are any of the aforementioned substituents, with ethylene carbonate, in the presence of a quaternary ammonium salt catalyst, wherein the quaternary ammonium salt has a structure (FIG. III)

in which

X⁻ is an inorganic or organic anion equivalent $R^3$,
$R^4$ may be $C_1$ to $C_{18}$ alkyl, $C_5$ to $C_6$ cycloalkyl, phenyl or benzyl,
$R^5$ may be a $C_1$ to $C_{18}$ alkyl or benzyl and,
$R^6$ may be $C_1$ to $C_{18}$ alkyl,
$R^3$ and $R^4$ may form a 5 member ring; or
$R^3$ and $R^4$ may form a 6 member ring, at elevated temperatures,
and subsequently isolating a finished product from said reaction mixture.

2. The process according to claim 1 wherein a quaternary ammonium halide is used as a catalyst.

3. The process according to claim 1 wherein tetraalkylammonium halides are used as catalysts.

4. The process according to claim 1 wherein benzyl trialkylammonium halides are used as catalysts.

5. The process according to claim 1 wherein from 0.1 to 0.001 moles of quaternary ammonium salt are used per mole of the 2,4-dihydroxybenzophenone starting material.

6. The process according to claim 1 wherein the reaction is carried out at temperatures from about 100° C. to about 210° C.

7. The process according to claim 1 wherein $R^1$ and $R^2$ (FIG. II) are both hydrogen.

8. The process according to claim 1 wherein $R^1$ (FIG. II) is an hydroxyl group in the ortho position relative to the carbonyl group.

9. The process according to claim 1 wherein $R^1$ (FIG. II) is a hydroxyl group in the ortho position relative to the carbonyl group and $R^2$ (FIG. II) a hydrogen in the para position relative to the carbonyl group.

10. The process according to claim 10 wherein $R^2$ (FIG. II) is an hydroxyl in the para position relative to the carbonyl group.

11. The process according to claim 1 wherein the reaction is carried out in the absence of a solvent.

12. The process according to claim 1 wherein from about 0.95 to about 1.5 moles of ethylene carbonate is used per mole of the 2,4-dihydroxy starting compound.

13. The process according to claim 1 wherein the 2-hydroxy-4-(2'-dihydroxyethoxy)benzophenone reaction product is isolated from the crude reaction mixture by adding water with stirring to said crude reaction mixture having a pH of about 10–12, adjusting said pH to about 7–8, and collecting said reaction product as a precipitate.

* * * * *